(12) United States Patent
van Esch et al.

(10) Patent No.: US 6,930,203 B2
(45) Date of Patent: Aug. 16, 2005

(54) GELLING AGENTS OR THICKENERS

(75) Inventors: Johannes Henricus van Esch, Groningen (NL); André Heeres, Groningen (NL)

(73) Assignee: Applied NanoSystems B.V., Groningen (NL)

( * ) Notice: Subject to any disclaimer, the term of this patent is extended or adjusted under 35 U.S.C. 154(b) by 1 day.

(21) Appl. No.: 10/656,839

(22) Filed: Sep. 5, 2003

(65) Prior Publication Data

US 2004/0097602 A1 May 20, 2004

Related U.S. Application Data

(63) Continuation of application No. PCT/NL02/00151, filed on Mar. 6, 2002.

(30) Foreign Application Priority Data

Mar. 6, 2001 (EP) .............................. 01200836

(51) Int. Cl.[7] .............................. C07C 233/05
(52) U.S. Cl. ................. 564/160; 564/158; 516/102; 536/4.1
(58) Field of Search ................. 564/158, 160; 516/102; 536/4.1

(56) References Cited

U.S. PATENT DOCUMENTS

| | | | |
|---|---|---|---|
| 2,084,626 A | 6/1937 | Tabern | |
| 5,112,601 A | 5/1992 | Sebag et al. | |
| 5,247,121 A | 9/1993 | Sebag et al. | |
| 5,329,044 A | 7/1994 | Kiely et al. | |
| 5,473,035 A | 12/1995 | Kiely et al. | |
| 5,478,374 A | 12/1995 | Kiely | |

FOREIGN PATENT DOCUMENTS

WO   WO 02/070463 A1   9/2002

OTHER PUBLICATIONS

Totton et al, J.Org Chem, vol. 22, p. 1104, 1957.*
Hoagland, The Formation of Intermediate Lactones During Amino–Lysis of Diethyl Galactarate, Carbohydrate Research, 1981, pp. 203–208, vol. 98.
Chemical Abstract, 1991, vol. 114, No. 1, XP002173886.
Database Beilstein 'Online! Abstract, XP002173887, 1993.
Database Beilstein 'Online! Abstract, XP002173888, 1992.
Database Beilstein 'Online! Abstract, XP002173889, 1957.
Database Beilstein 'Online! Abstract, XP002173890, 1966.
Database Beilstein 'Online! Abstract, XP002173891, 1949.
Database Beilstein 'Online! Abstract, XP002173892, 1887.
PCT International Search Report, PCT/NL02/00151, dated Apr. 24, 2002.
Kurtz et al., Saccharolactane as a Reagent for Precipitating Certain Amines, J. Biol. Chem., 1939, pp. 693–699.

* cited by examiner

*Primary Examiner*—Shailendra Kumar
(74) *Attorney, Agent, or Firm*—TraskBritt

(57) ABSTRACT

The present invention relates to a novel class of gelling agents or thickeners, to a process for preparing gelling agents or thickeners and to their use to prepare the gels. The present gelling agents or thickeners have the form of an N,N'-disubstituted aldaramide or N,N'-disubstituted pentaramide.

19 Claims, 1 Drawing Sheet

GELLING AGENTS OR THICKENERS

CROSS-REFERENCE TO RELATED APPLICATION

This application is a continuation of PCT International Patent Application PCT/NL02/00151, filed Mar. 6, 2002, designating the United States and published, in English, as International Publication Number WO 02/070463 A1, filed Sep. 12, 2002, the contents of which are incorporated by this reference.

TECHNICAL FIELD

The present invention relates to a novel class of gelling agents, a process for producing them and to their application in preparing gels for various applications.

BACKGROUND

Thermally reversible gelling or thickening of organic solvents by low molecular weight compounds are of particular interest for hardeners of spilled fluids and cooking oils, thickeners for paints, cosmetic materials and several other technical applications. The self assembly of these gelator/thickener molecules occurs by means of noncovalent interactions such as hydrophobic interaction, π—π interactions, electronic interactions, hydrogen bonding or combinations thereof. Although several gelator/thickener molecules have been identified during the last decade, there is still interest in stable gelator/thickeners that can be synthesized easily from cheap, renewable sources and gelate or thicken a wide variety of solvents.

BRIEF SUMMARY OF THE INVENTION

Figure 1:
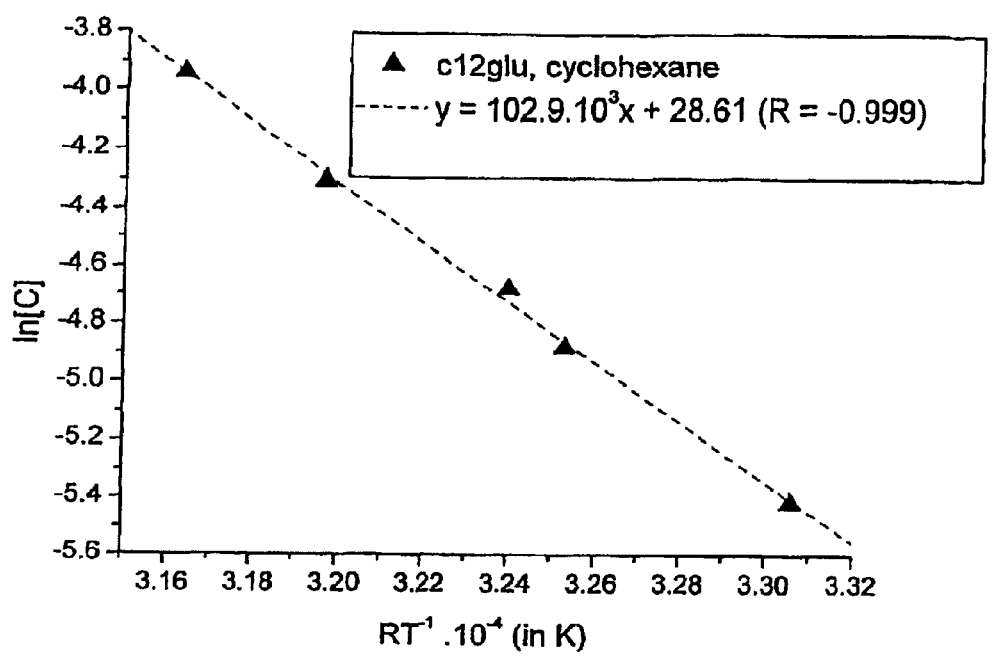
FIG. 1 depicts a phase diagram of 5 (C6-Glu-C6) and 15 (C12-Glu-C12) determined with the dropping ball method.
Figure 1:
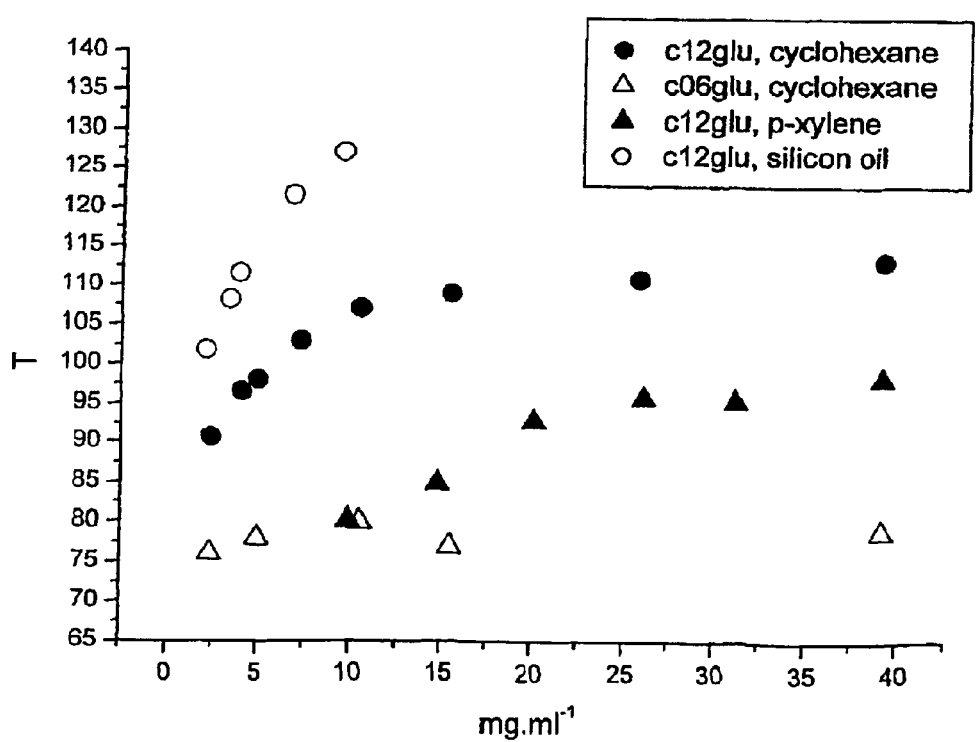

The present invention includes a novel class of gelling agents or thickeners. The present invention provides gelling agents or thickeners that are based on readily available and economically attractive starting materials. The present invention also provides gelling agents or thickeners capable of gelling or thickening a wide variety of solvents, making the gelling agents or thickeners suitable for employment in various applications.

The invention includes preparing gelling agents or thickeners from low molecular carbohydrates. The present invention relates to a gelling agent in the form of N,N'-disubstituted aldaramides and N,N'-disubstituted pentaramides and derivatives thereof. Specifically, the present invention relates to a gelling agent having the following structure:

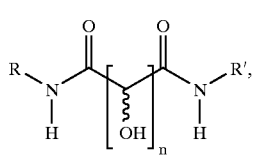

(I)

wherein n is 3 or 4, and wherein R and R' represent the same or different substituents chosen from the group of substituted or unsubstituted, branched, possibly aromatic, groups containing cyclic or linear alkyl, alkenyl, alkynyl groups having from 1 to 40 carbon atoms.

BEST MODE OF THE INVENTION

In a preferred embodiment, R and R' each represent, independently, a linear, branched, or cyclic alkyl group having 4–20 carbon atoms. More preferred is that R and R' each are independently selected from the group of cycloalkyl groups having 4–16 carbon atoms. In a preferred embodiment, R and R' represent the same substituent.

One advantage of the present invention is that gelling agents or thickeners can be based on naturally occurring products, such as carbohydrates. Thus, the starting materials for producing them are from a renewable source.

A gelling agent or thickener according to the present invention may be prepared by converting an aldose or pentose to its corresponding aldaric or pentaric acid, or a salt thereof, such as an alkali metal salt or an (alkyl)ammonium salt. It is preferred to use an aldose or pentose chosen from the group of allose, altrose, glucose, mannose, gulose, idose, galactose, talose, ribose, arabinose, xylose, lyxose and derivatives thereof, as these lead to products having particularly favorable gelling and/or thickening properties. It is to be noted that both the L and the D isomers of the aldose or pentose, as well as mixtures thereof, can be used. Suitable derivatives of the mentioned aldoses and pentoses include deoxy aldoses or pentoses, ethers, esters and the like. In a more preferred embodiment, D-glucose is chosen as aldose.

The conversion of the aldose or pentose to its corresponding aldaric or pentaric acid is generally achieved by oxidation. The oxidation can suitably be carried out using $Pt/O_2$, TEMPO/NaOCl/(NaBr) or $HNO_3/(NaNO_2)$ as an oxidizing agent. Further details for the manner in which the oxidation may be carried out can be found in U.S. Pat. Nos. 5,831,043, 5,599,977 and 6,049,004, and in *J. Org. Chem.*, 1977, 42, 3562–3567; J-F. Thaburet et al., *Carbohydr. Res.* 330 (2001), 21–29, all of which are incorporated herein by reference.

The thus obtained aldaric or pentaric acid or salt thereof is subsequently condensed with a primary amine to obtain the objective gelling agent or thickener.

The aldaric or pentaric acid can be condensed with an amount of at least 200 mole %, with respect to the aldaric or pentaric acid, of a primary amine. It is preferred to activate the aldaric or pentaric acid first by means of lactonization and/or esterification, depending on the stereochemistry of the carbohydrate. Further details may be found in Kurtz et al., *J. Biol. Chem.*, 1939, 693–699; Hoagland, *Carbohydrate Res.*, 1981, 98, 203–208, and U.S. Pat. No. 5,312,967, which are incorporated herein by reference.

In an alternative embodiment, nonsymmetrical N,N'-dialkylaldaramides or N,N'-dialkylpentaramides may be prepared, wherein R and R' represent different substituents. In accordance with this embodiment, the aldaric or pentaric acid may be converted into an N-alkyl-1-aldar/pentaramid-6-ate or N-alkyl-6-aldar/pentaramid-1-ate (as disclosed in U.S. Pat. No. 5,239,044; L. Chen et al., *J. Org. Chem.*, 61 (1996) 5847–5851; R. Lee et al., *Carbohydr. Res.* 64 (1978) 302–308; and K. Hashimoto et al., *J. Polym. Sci. Part A, Polym. Chem.*, 37 (1999) 303–312), activated and subsequently condensed with, preferably 100 mole % with respect to the N-alkyl aldar/pentar-ate, of a second primary amine.

In general, the obtained gelling agent or thickener precipitates from the reaction mixture in which it is formed and can be easily isolated by filtration. Further purification can be performed by conventional techniques like crystallization or, in the case of products based on galactaric acid derivatives, by thoroughly washing with ethanol, water, acetone or hexane.

It will be understood that the use of the present gelling agents or thickeners to prepare a gel or to thicken a composition is also encompassed by the invention. As is well known, gelling behavior of compounds or compositions is highly unpredictable. In principle, a solution of a specific compound in a solvent, e.g. an organic solvent, is considered a gel when a homogeneous substance is obtained which exhibits essentially no gravitational flow. Preferably, the gelling phenomenon is thermo reversible. However, in so far as the present compounds do not provide a gel in a composition, they may be used as a thickener or rheology controlling agent, as their addition to a composition may give rise to an increase in viscosity of the composition.

Compositions in which the present compound has been found to produce a gel include compositions in numerous solvents. Preferred examples include aromatic and nonaromatic hydrocarbons, alcohols, ethers, esters, aldehydes, alkanoic acids, epoxides, amines, halogenated hydrocarbons, silicon oils, vegetable oils, phosphoric esters, sulfoxides, water and mixtures thereof. In order to obtain a gel, the gelling agent or thickener is preferably mixed with the composition to be transformed to a gel in an amount of between 0.01 and 50 wt. %, based on the weight of the composition. In a preferred embodiment, the mixture of the gelling agent or thickener and the composition is heated to allow for an even better gel formation or thickening. Typically, the heating will involve raising the temperature of the mixture to about 30–175° C. until a clear solution is obtained. In an alternative embodiment, the gelling agent is first dissolved in a polar or apolar solvent and then added to or sprayed into a composition or solvent to be converted into a gel.

The resultant gel or thickened composition, which is also encompassed by the present invention, may find use in one of numerous applications. It is conceived that such applications lie in the field of cosmetics, oil recovery (e.g. from the sea), food products, transport of industrial solvents, stabilization of organic solvents under near zero gravity conditions, stiffening of fuels to increase stability and reduce fluidity, lubricants, coatings, printing inks, and adhesives. In these applications, they may be used analogous to conventional gelling agents or thickeners, which they replace.

The invention will now be further elucidated by the following, illustrative examples.

EXAMPLES

Synthesis of Starting Materials

Potassium hydrogen D-glucarate (R. L. Whistler, M. L. Wolfrom, J. N. BeMiller, *Methods in Carbohydrate Chemistry*, Vol. II (1963), Academic Press Inc., 47–48), D-glucaric acid (lactone) (L. Chen, D. E. Kiely, *J. Org. Chem.*, 61 (1996) 5847–5851), D-glucaro-6,3-lactone (L. Chen, D. E. Kiely, *J. Org. Chem.*, 61 (1996) 5847–5851), D-mannaric acid dilactone (E. Fischer, Berichte, 24 (1891) 539–546), diethyl galacterate (R. L. Whistler, M. L. Wolfrom, J. N. BeMiller, *Methods in Carbohydrate Chemistry, Vol. II* (1963), Academic Press Inc., 40–41), D-ribaric acid (lacton) (C. E. Cantrell, D. E. Kiely, G. J. Abruscato, J. M. Riordan, *J. Org. Chem.*, 42 (1977) 3562–3567, as described for D-xylaric acid, R. E. Gall, L. Tarasoff, *Aust. J. Chem.*, 28 (1975) 687–691) were synthesized according to literature procedures.

Cyclohexylammonium 6-(N-cyclohexyl)-D-glucaramide-1-ate.

D-glucaro 6,3-lacton (1.04 g, 5.4 mmol) was added to a solution of cyclohexylamine (1.34 g, 13.5 mmol) in EtOH (50 ml). After 20 hours stirring, the precipitate was filtered off and crystallized from EtOH. Yield 0.97 g (2.5 mmol, 46%). $^1$H-NMR ($d_6$-DMSO, 300 MHz, ppm, δ 1.10–1.38 (m, 10H), 1.45–1.90 (m, 10H), 2.91 (m, 1H), 3.55 (m, 1H), 3.65 (m, 2H), 3.78 (t, 1H), 3.89 (d, 1H), 7.55 (d, 1H). $^{13}$C-NMR (d6-DMSO, 300 MHz, ppm): 24.54, 25.23, 25.32, 25.85, 31.28, 32.86, 32.93, 47.88, 49.82, 71.60, 72.45, 72.80, 73.27, 172.70, 176.36. Anal Calculated for $C_{18}H_{34}N_2O_7$: C, 55.37; H, 8.78, N, 7.17. Found: C, 55.22; H, 8.76; N, 7.37.

Synthesis of 3-O-methyl diethyl D-glucaric Acid.

3-O-Methyl-∀,∃-D-glucose (7.00 g, 36 mmol) was added in portions (in 45 minutes) to a solution of $NaNO_2$ (0.010 g, 0.14 mmol) in $HNO_3$ (15 ml, 65%) at T=50–55° C. After 45 minutes T=50° C., the reaction was cooled to RT, and stirred for another 30 minutes. EtOH (40 ml) was added in portions and the reaction mixture was stripped with EtOH several times using a rotavap. The crude reaction mixture was distilled (Kugelrohr) and the fraction of b.p. 225° C./0.4 mm Hg was collected. Yield 4.74 g (16.9 mmol, 47%). $^1$H-NMR ($d_6$-DMSO, 300 MHz, ppm, δ 1.20 (t, 6H), 3.31 (s, 3H), 4.10 (m, 4H+1H), 4.35 (m, 1H), 4.49 (m, 1H), 4.94 (t, 1H). $^{13}$C-NMR ($d_6$-DMSO, 300 MHz, ppm): 15.09, 59.50, 61.47, 69.96, 71.81, 78.06, 83.89, 171.47, 176.02.

Synthesis of Citronellylamine.

1) Preparation of 3,7-dimethyl-oct-6-enal oxim. Citronellal (15.37 g, 100 mmol) in EtOH (300 ml) was added to a solution of $NH_2OH$ (7.00 g, 100 mmol) and NaOH (4.07 g, 102 mmol) in $H_2O$ (100 ml) and stirred for 20 hours at T=60° C. After evaporation, the remaining oil was dissolved in $H_2O$, acidified with 2M HCl, and subsequently extracted with $Et_2O$ (2×). After drying with $Na_2SO_4$ filtration and evaporation, crude 3,7-dimethyl-oct-6-enal oxim (mixture of cis/trans) was isolated. Yield 14.89 g (88 mmol, 88%). $^1$H-NMR ($CDCl_3$, 300 MHz, ppm, δ 0.88 (t, 3H), 1.11–1.34 (m, 2H), 1.54 (s, 3H), 1.62 (s, 3H), 1.94–2.30 (m, 5H), 5.01 (t, 1H), 6.69 (t, 0.5H), 7.36 (0.5H). $^{13}$C-NMR ($CDCl_3$, 300 MHz, ppm): 15.12, 16.92, 17.21, 22.89, 22.95, 23.18, 27.98, 28.42, 29.47, 33.88, 34.11, 34.32, 121.79, 121.84, 128.96, 148.91.

2) Preparation of Citronellylamine. 3,7-Dimethyl-oct-6-enal oxim (mixture of cis/trans 1:1, 14.54 g, 68 mmol) was added slowly to 173 ml of a solution of 1M $LiAlH_4$ in THF under $N_2$ atmosphere. After 20 hours refluxing, the suspension was decanted and the precipitate was washed with $Et_2O$ (3×). After drying of the $Et_2O$/THF layer with $Na_2SO_4$, filtration and evaporation of the solvent, the remaining oil was distilled under reduced pressure (0.8–1.0 mm Hg, T=65° C.). Yield 5.00 g (32.4 mmol, 37%). $^1$H-NMR ($CDCl_3$, 300 MHz, ppm, δ 0.88 (d, 3H), 0.92–1.44 (m, 7H), 1.50 (s, 3H), 1.58 (s, 3H), 1.88 (m, 2H), 2.62 (m, 2H), 5.00 (t, 1H). $^{13}$C-NMR ($CDCl_3$, 300 MHz, ppm): 15.07, 17.00, 22.94, 23.15, 27.57, 34.67, 37.57, 38.68, 122.27, 128.57.

Synthesis of 8-amino-pentadecane.

1) Preparation of pentadecan-8-one oxim. Dihexylketone (13.47 g, 68 mmol) in EtOH (300 ml) is added to a solution of $NH_2OH$ (4.74 g, 68 mmol) and NaOH (2.74 g, 69 mmol) in $H_2O$ (100 ml) and stirred for 20 hours at T=60° C. After evaporation, the remaining oil is dissolved in $H_2O$, acidified with 2M HCl, and subsequently extracted with $Et_2O$ (2×). After drying with $Na_2SO_4$ filtration and evaporation, crude pentadecan-8-one oxim (mixture of cis/trans 1:1) was isolated. Yield 13.57 g (64 mmol, 93%). $^1$H-NMR ($CDCl_3$, 300 MHz, ppm, δ 0.83 (t, 6H), 1.25 (m, 8H), 1.45 (m, 4H), 2.11 (t, 2H), 2.28 (t, 2H). $^{13}$C-NMR ($CDCl_3$, 300 MHz, ppm): 11.56, 20.06, 23.13, 23.76, 25.99, 26.51, 27.07, 29.09, 31.61, 159.57.

2) Preparation of 8-amino-pentadecane. Pentadecan-8-one oxim (mixture of cis/trans 1:1, 13.45 g, 63 mmol) was added slowly to 127 ml of a solution of 1M LiAlH$_4$ in THF under N$_2$ atmosphere. After 20 hours refluxing, the suspension was decanted and the precipitate was washed with Et$_2$O (3×). After drying of the Et$_2$O/THF layer with Na$_2$SO$_4$, filtration and evaporation of the solvent, the remaining oil was distilled under reduced pressure (0.8–1.0 mm Hg, T=105° C.). Yield 5.17 g (26.1 mmol, 41%). $^1$H-NMR (CDCl$_3$, 300 MHz, ppm, δ 0.79 (d, 6H), 1.18–1.30 (m, 20H), 2.58 (m, 1H). $^{13}$C-NMR (CDCl$_3$, 300 MHz, ppm): 11.53, 20.09, 23.62, 26.97, 29.35, 35.67, 48.67.

Example 1

Synthesis of dibutyl D-glucaramicle. D-Glucaric acid (lactone) (1.43 g, about 7.1 mmol) was added to a solution of butylamine (1.34 g, 17.9 mmol) in EtOH (30 ml). After 20 hours stirring, the precipitate was filtered off and crystallized from EtOH (yield 0.31 g, 1.0 mmol, 14%). $^1$H-NMR (d$_6$-DMSO, 300 MHz, ppm): δ 0.87 (t, 6H), 1.28 (m, 4H), 1.40 (m, 4H), 3.08 (m, 4H), 3.69 (bs, 1H, H$_4$), 3.88 (bs, 1H, H$_3$), 3.92 (bs, 1H, H$_5$), 3.98 (bs, 1H, H$_2$), 4.61 (d, 1H, OH$_3$), 4.74 (d, 1H, OH$_4$), 5.35 (d, 1H, OH$_2$), 5.52 (d, 1H, OH$_5$), 7.59 (t, 1H, NH$_1$), 7.84 (t, 1H, NH$_6$). $^{13}$C-NMR (d6-DMSO, 300 MHz, ppm): 14.65, 20.45, 32.21, 38.83, 71.33, 72.50, 73.95, 74.21, 173.01, 173.98, Anal Calculated for C$_{14}$H$_{28}$N$_2$O$_6$: C, 52.48; H, 8.81, N, 8.74. Found: C, 52.06; H, 8.79; N, 8.61.

Example 2

Synthesis of dibutyl D-mannaramide. D-Mannaric acid dilactone (0.61 g, 3.5 mmol) is added to a solution of butylamine (0.81 g, 10.8 mmol) in EtOH (20 ml). After 20 hours stirring, the precipitate was filtered off and crystallized from EtOH (yield 0.38 g, 1.2 mmol, 34%). $^1$H-NMR (d$_6$-DMSO, 300 MHz, ppm): δ 0.87 (t, 6H), 1.24 (m, 4H), 1.39 (m, 4H), 3.09 (q, 4H), 3.70 (t, 2H, H$_3$, H$_4$), 3.88 (t, 2H, H$_2$, H$_5$), 4.79 (d, 2H, OH$_3$, OH$_4$), 5.42 (d, 2H, OH$_2$, OH$_5$), 7.84 (t, 2H, NH$_1$, NH$_6$). $^{13}$C-NMR (d$_6$-DMSO, 300 MHz, ppm): 14.64, 20.45, 32.13, 38.59, 72.09, 72.37, 174.36. Anal Calculated for C$_{14}$H$_{28}$N$_2$O$_6$: C, 52.48; H, 8.81, N, 8.74. Found: C, 52.07; H, 8.79; N, 8.65.

Example 3

Synthesis of dibutyl galactaramide. Diethyl galactarate (2.00 g, 7.5 mmol) was added to a solution of butylamine (1.40 g, 18.8 mmol) in EtOH (30 ml). After 20 hours stirring, the precipitate was filtered off and crystallized from DMSO/H$_2$O (yield 0.30 g, 0.9 mmol, 13%). $^1$H-NMR (d$_6$-DMSO, 300 MHz, ppm): δ 0.88 (t, 6H), 1.29 (m, 4H), 1.40 (m, 4H), 3.11 (m, 4H), 3.78 (s, 2H, H$_3$, H$_4$), 4.11 (s, 2H, H$_2$, H$_5$), 4.39 (bs, 2H, OH$_3$, OH$_4$), 5.23 (bs, 2H, OH$_2$, OH$_5$), 7.55 (t, 2H, NH$_1$, NH$_6$). $^{13}$C-NMR (d$_6$-DMSO, 300 MHz, ppm): 14.67, 20.41, 32.32, 38.86, 71.57, 174.07. Anal Calculated for C$_{14}$H$_{28}$N$_2$O$_6$: C, 52.48; H, 8.81, N, 8.74. Found: C, C, 51.58; H, 8.88; N, 8.50.

Example 4

Synthesis of dicyclohexyl D-ribaramide. D-Ribaric acid (lacton) (0.32 g, 2.0 mmol) was added to a solution of NEt$_3$ (0.25 ml) and cyclohexylamine (0.45 g, 4.5 mmol) in EtOH (20 ml). After 20 hours stirring, the solution was cooled to T=4° C. and filtered. Yield 0.14 g (0.41 mmol, 20%). $^1$H-NMR (d$_6$-DMSO, 500 MHz, T=100° C., ppm): δ 1.27 (m, 10H), 1.70 (m, 10H), 3.59 (bs, HDO+1H), 3.97 (s, 2H), 7.52 (d, 1H, NH$_6$). $^{13}$C-NMR (d$_6$-DMSO, 300 MHz, ppm): 25.90, 26.38, 33.42, 48.59, 73.24, 75.98, 173.12. Anal Calculated for C$_{17}$H$_{30}$N$_2$O$_5$: C, 59.63; H, 8.83, N, 8.18. Found: C, 59.30; H, 9.05; N, 8.03.

Example 5

Synthesis of dicyclohexyl D-glucaramide. D-Glucaro 6,3 lactone (1.07 g, 5.6 mmol) was added to a solution of p-toluene sulfonic acid (0.042 g, 0.22 mmol) in EtOH (20 ml). At T=50° C. cyclohexylamine (1.10 g, 11.1 mmol) is dropped slowly to the solution. After one hour stirring, the solution was cooled to RT and H$_2$O (20 ml) was added. Evaporation till 10–15 ml gave a white precipitate which was filtered off and crystallized from EtOH (yield 0.89 g, 2.1 mmol, 38%). $^1$H-NMR (d$_6$-DMSO, 300 MHz, ppm): δ 1.26 (m, 10H), 1.69 (m, 10H), 3.56 (bs, 2H), 3.68 (bs, 1H), 3.89 (bs, 2H), 3.96 (s, 1H), 4.61 (d, 1H), 4.69 (d, 1H), 5.36 (d, 1H), 5.45 (d, 1H), 7.31 (d, 1H, NH$_1$), 7.58 (d, 1H, NH$_6$). $^{13}$C-NMR (d6-DMSO, 300 MHz, ppm): 25.57, 26.07, 33.16, 48.10, 48.25, 71.34, 72.57, 73.85, 74.04, 172.17, 172.98. Anal Calculated for C$_{18}$H$_{32}$N$_2$O$_6$: C, 58.05; H, 8.66, N, 7.52. Found: C, 58.11; H, 8.76; N, 7.46.

Example 6

Synthesis of dicyclohexyl D-mannaramide. D-Mannaric acid dilactone (0.45 g, 2.3 mmol) was added to a solution of cyclohexylamine (0.58 g, 5.9 mmol) in EtOH (20 ml). After 20 hours stirring, the solution was refluxed for two hours and after cooling the precipitate was filtered off and crystallized from EtOH (yield 0.05 g, 0.13 mmol, 6%). $^1$H-NMR (d$_6$-DMSO, 300 MHz, ppm): δ 1.24 (m, 10H), 1.70 (m, 10H), 3.59 (bs, 2H), 3.69 (t, 2H), 3.86 (t, 2H), 4.72 (d, 2H), 5.34 (d, 2H), 7.62 (d, 2H, NH). $^{13}$C-NMR (d$_6$-DMSO, 300 MHz, ppm): 25.52, 26.10, 33.16, 48.26, 71.96, 72.27, 173.36. Anal Calculated for C$_{14}$H$_{28}$N$_2$O$_6$: C, 58.05; H, 8.66, N, 7.52. Found: C, 57.80; H, 8.74; N, 7.37.

Example 7

Synthesis of dicyclohexyl galactaramide. Diethyl galacterate (2.66 g, 10.0 mmol) was added to a solution of cyclohexylamine (2.68 g, 27.0 mmol) in EtOH (50 ml). After 20 hours stirring, the suspension was refluxed for three hours and after cooling the precipitate was filtered off, washed with H$_2$O/aceton 9:1 (3×25 ml) and H$_2$O (50 ml) and crystallized from DMSO (yield 0.84 g, 2.3 mmol, 23%). $^1$H-NMR (d$_6$-DMSO, 300 MHz, ppm): δ 1.24 (m, 10H), 1.71 (m, 10H), 3.60 (bs, 2H), 3.76 (d, 2H), 4.09 (d, 2H), 4.38 (d, 2H), 5.18 (d, 2H), 7.26 (d, 2H, NH). $^{13}$C-NMR (d$_6$-DMSO, 300 MHz, ppm): 25.08, 25.82, 32.95, 47.87, 71.39, 71.60, 172.74. Anal Calculated for C$_{14}$H$_{28}$N$_2$O$_6$: C, 58.05; H, 8.66, N, 7.52. Found: C, 57.88; H, 8.74; N, 7.42.

Example 8

Synthesis of dioctyl D-glucaramide. D-Glucaric acid (lactone) (1.35 g, about 7.0 mmol) was added to a solution of octylamine (1.85 g, 14.0 mol) in EtOH (30 ml). After 20 hours stirring, the suspension was refluxed for three hours and after cooling the precipitate was filtered off and. recrystallized twice from EtOH (yield 0.57 g, 1.3 mmol, 19%). $^1$H-NMR (d$_6$-DMSO, 500 MHz, COSY, T=50° C., ppm): δ 0.83 (t, 6H, 1.22 (m, 20H), 1.37 (m, 4H), 3.04 (m, 4H), 3.65 (m, 1H, H$_4$), 3.82 (m, 1H, H$_3$), 3.88 (m, 1H, H$_5$), 3.94 (m, 1H, H$_2$), 4.56 (d, 1H, J=6.9 Hz, OH$_3$), 4.70 (d, 1H, J=4.7 Hz, OH$_4$), 5.31 (d, 1H, J=5.2 Hz, OH$_2$), 5.48 (d, 1H, J=6.3 Hz, OH$_5$), 7.56 (t, 1H, J=5.9 Hz, NH$_1$), 7.80 (t, 1H, J=5.9 Hz, NF$_6$). $^1$H-NMR (d$_6$-DMSO, 500 MHz, COSY, 1 drop D$_2$O added, T=50° C. ppm): δ 0.83 (t, 6H), 1.22 (m, 20H), 1.37 (m, 4H), 3.04 (m, 4H), 3.65 (dd, 1H, J$_{4,5}$=6.2 Hz, J$_{3,4}$=3.5 Hz, H$_4$), 3.82 (t, 1H, J$_{2,3}$=3.7 Hz, H$_3$), 3.88 (d, 1H, H$_5$), 3.94 (d, 1H, H$_2$), $^{13}$C-NMR (d$_6$-DMSO, 300 MHz, HMQC, T=50° C., ppm): 14.65, 22.80, 27.10, 29.47, 29.72, 29.82, 31.98, 38.97, 71.08, 72.37, 73.55, 73.66, 172.70, 173.60. Anal Calculated for C$_{22}$H$_{44}$N$_2$O$_6$: C, 61.08; H, 10.25, N, 6.48. Found: C, 60.94; H, 10.41; N, 6.42.

Example 9

Synthesis of dioctyl D-mannaramide. D-Mannaric acid dilactone (2.14 g, 12.3 mmol) is added to a solution of octylamine (3.10 g, 5.9 mmol) in EtOH (50 ml). After 20 hours stirring, the suspension was refluxed for one hour and after cooling the precipitate was filtered off and crystallized from EtOH (yield 1.59 g, 3.7 mmol, 30%). $^1$H-NMR (d$_6$-DMSO, 300 MHz, ppm): δ 0.87 (t, 6H), 1.25 (m, 20H), 1.42 (m, 4H), 3.08 (m, 4H), 3.70 (t, 2H), 3.88 (t, 2H), 4.79 (d, 2H), 5.41 (d, 2H), 7.87 (d, 2H, NH). $^{13}$C-NMR (d$_6$-DMSO, 300 MHz, ppm): 14.91, 23.05, 27.31, 29.62, 29.99, 32.23, 39.28, 72.05, 72.38, 174.3. Anal Calculated for C$_{22}$H44N$_2$O$_6$: C, 61.08; H, 10.25, N, 6.48. Found: C, 60.84; H, 10.39; N, 6.40.

Example 10

Synthesis of dioctyl galactaramide. Diethyl galacterate (2.66 g, 10.0 mmol) was added to a solution of octylamine (2.64 g, 20.5 mmol) in EtOH (50 ml). After 20 hours stirring, the precipitate was filtered off and crystallized from DMSO (yield 3.00 g, 6.9 mmol, 69%). $^1$H-NMR (d$_6$-DMSO, 300 MHz, ppm): δ 0.90 (bs, 6H), 1.30 (bs, 20H), 1.48 (bs, 4H), 3.14 (bs, 4H), 3.82 (bs, 2H), 4.08 (bs, 2H), 4.17 (bs, 2H), 4.85 (bs, 2H), 7.33 (bs, 2H, NH). $^{13}$C-NMR (d$_6$-DMSO, 300 MHz, ppm): 14.11, 22.37, 26.82, 28.95, 29.11, 29.61, 31.60, 38.97, 71.45, 173.34. Anal Calculated for C$_{22}$H$_{44}$N$_2$O$_6$: C, 61.08; H, 10.25, N, 6.48. Found: C, 61.15; H, 10.47; N, 6.44.

Example 11

Synthesis of dicitronellyl D-glucaramide. D-Glucaric acid (lactone) (2.90 g, about 14.0 mmol) was added to a solution of citronellylamine (5.00 g, 32.4 mmol) in EtOH (40 ml). After 20 hours stirring, the suspension was refluxed for three hours and after cooling, the precipitate was filtered off and recrystallized from 2-PrOH. Yield 2.30 g (4.8 mmol, 33%). $^1$H-NMR (d$_6$-DMSO, 500 MHz, ppm): δ 0.86 (d, 6H), 1.09–1.45 (m, 10H), 1.58 (s, 6H), 1.66 (s, 6H), 1.95 (m, 4H), 3.12 (m, 4H), 3.71 (bs, 1H), 3.89 (bs, 1H), 3.92 (bs, 1H), 3.98 (bs, 1H), 4.63 (bs, 1H, 4.77 (bs, 1H), 5.10 (t, 2H), 5.35 (bs, 1H), 5.55 (bs, 1H), 7.57 (t, 1H), 7.84 (t, 1H). $^{13}$C-NMR (d$_6$-DMSO, 300 MHz, ppm): 18.45, 20.15, 25.84, 26.44, 30.57, 36.99, 37.09, 37.25, 37.32, 37.53, 71.32, 72.47, 73.89, 74.18, 125.60, 131.37, 172.92, 173.97. Anal Calculated for C$_{26}$H$_{48}$N$_2$O$_6$: C, 64.43; H, 9.98, N, 5.78. Found: C, 64.13; H, 10.02; N, 5.75.

Example 12

Synthesis of didodecyl D-glucaramide. D. Glucaric acid (lactone) (0.81 g, about 3.9 mmol) was added to a solution of dodecylamine (1.94 g, 10.5 mmol) in EtOH (25 ml). After 72 hours stirring, the suspension was refluxed for three hours and after cooling, the precipitate was filtered off and recrystallized from DMSO. Yield 1.30 g (2.4 mmol, 61%). $^1$H-NMR (d$_6$-DMSO, 300 MHz, T=100° C., ppm.): δ 0.89 (t, 6H), 1.29 (m, 36H), 1.47 (t, 4H), 3.13 (m, 4H), 3.75 (m, 1H), 3.92 (m, 1H), 3.97 (m, 1H), 3.99 (m, 1H), 4.50 (bs, 2H), 5.05 (bs, 2H), 7.30 (t, 1H), 7.53 (t, 1H). $^{13}$C-NMR (d$_6$-DMSO, 300 MHz, T=100° C., ppm): 14.07, 22.34, 26.79, 28.99, 29.12, 29.33, 31.63, 38.86, 71.15, 72.41, 73.37, 73.55, 172.37, 173.41. Anal Calculated for C$_{30}$H$_{60}$N$_2$O$_6$: C, 66.14; H, 11.10, N, 5.14. Found: C, 66.14; H, 11.05; N, 5.12.

Example 13

Synthesis of didodecyl D-mannaramide. D-Mannaric acid dilactone (0.43 g, 2.5 mmol) was added to a solution of dodecylamine (1.12 g, 6.1 mmol) in EtOH (20 ml). After 72 hours stirring, the precipitate was filtered off and crystallized from DMSO (yield 0.35 g, 3.7 mmol, 26%). $^1$H-NMR (d$_6$-DMSO, 300 MHz, T=100° C., ppm): δ 0.89 (t, 6H), 1.29 (m, 36H), 1.47 (t, 4H), 3.14 (m, 4H), 3.77 (d, 2H), 3.95 (d, 2H), 4.61 (bs, 2H), 5.08 (bs, 2H), 7.54 (t, 1H). $^{13}$C-NMR (d$_6$-DMSO, 300 MHz, T=100° C., ppm): 14.05, 22.35, 26.77, 28.98, 29.11, 29.34, 31.63, 38.96, 71.96, 72.31, 173.60. Anal Calculated for C$_{30}$H$_{60}$N$_2$O$_6$: C, 66.14; H, 11.10, N, 5.14. Found: C, 65.76; H, 11.01; N, 5.11.

Example 14

Synthesis of didodecyl galactaramide. Diethyl galacterate (2.66 g, 10.0 mmol) was added to a solution of dodecylamine (3.75 g, 20.5 mmol) in EtOH (50 ml). After 72 hours stirring, the precipitate was filtered (yield 4.87 g, 8.9 mmol, 89%). Owing to the low solubility in several solvents tested, no proper NMR spectra could be obtained.

Example 15

Synthesis of dicyclododecyl D-glucaramide. D-Glucaro 6,3-lacton (7.67 g, 40.0 mmol) was added to a solution of cyclododecylamine (14.93 g, 81.6 mmol) in 2-methoxyethanol (125 ml). The reaction mixture was heated slowly till T=120° C. in three hours and kept at this T for four hours. After cooling, the precipitate was filtered off and recrystallized from DMSO and EtOH. Yield 9.50 g (17.6 mmol, 44%). $^1$H-NMR (d$_6$-DMSO, 300 MHz, T=100° C., ppm): δ 1.36 (m, 36H), 1.60 (m, 4H), 3.75 (m, 1H), 3.97 (m, 5H), 4.47 (bs, 2H), 6.98 (bs, 1H), 7.21 (bs, 1H). $^{13}$C-NMR (d$_6$-DMSO, 300 MHz, T=100° C., ppm): 22.03, 23.97, 24.14, 30.59, 45.45, 71.21, 72.32, 73.33, 73.71, 171.76, 172.76. Anal Calculated for C$_{30}$H$_{56}$N$_2$O$_6$: C, 66.63; H, 10.44, N, 5.18. Found: C, 67.00; H, 11.30; N, 4.97.

Example 16

Synthesis of dicyclododecyl D-mannaramide. D-Mannaric acid. dilactone (1.99 g, 11.4 mmol) was added to a solution of cyclododecylamine (0.58 g, 5.9 mmol) in EtOH (20 ml). After 20 hours stirring, the solution was refluxed for two hours and after cooling, the precipitate was filtered off and crystallized from EtOH and DMSO (yield 0.51 g, 0.94 mmol, 10%). $^1$H-NMR (d$_6$-DMSO, 300 MHz, T=100° C., ppm): δ 1.36 (m, 36H), 1.61 (m, 8H), 3.75 (bs, 2H), 3.93 (bs, 4H), 4.58 (bs, 2H), 5.07 (bs, 2H), 7.24 (d, 2H, NH). $^{13}$C-NMR (d$_6$-DMSO, 300 MHz, T=100° C., ppm): 22.05, 23.99, 24.17, 30.62, 45.68, 72.23, 173.01. Anal Calculated for C$_{30}$H$_{56}$N$_2$O$_6$.0.25 C$_2$H$_6$SO: C, 65.01; H, 10.46, N, 5.05. Found: C, 65.08; H, 10.29; N, 5.05.

Example 17

Synthesis of dicyclododecyl galactaramide. Diethyl galacterate (2.67 15 g, 10.0 mmol) was added to a solution of cyclododecylamine (3.78 g, 20.7 mmol) in EtOH (50 ml). After 48 hours stirring, the precipitate was filtered and washed with H$_2$O and EtOH (yield 2.43 g, 4.5 mmol, 45%). Owing to the low solubility in several solvents tested, no proper NMR spectra could be obtained.

Example 18

Synthesis of di-8-pentadecyl D-glucaramide. D-Glucaric acid (lactone) (2.53 g, about 12.7 mmol) is added to a solution of 8-aminopentadecane (5.17 g, 26.1 mmol) in EtOH (35 ml). After 20 hours stirring, the suspension was refluxed for 20 hours and recrystallized from EtOH/H$_2$O (3×). Yield 0.72 g (1.3 mmol, 10%). $^1$H-NMR (d$_6$-DMSO, 300 MHz, ppm): δ 0.86 (t, 12H), 1.23 (m, 32H), 1.36 (t, 8H), 3.69 (bs, 3H), 3.88 (bs, 1H), 3.94 (bs, 1H), 3.99 (m, 1H), 4.56 (bs, 1H), 4.71 (bs, 1H), 5.33 (bs, 1H), 5.47 (bs, 1H), 7.15 (d, 1H), 7.41 (d, 1H). $^{13}$C-NMR (d$_6$-DMSO, 300 MHz, T=100° C., ppm); 14.86, 23.03, 26.37, 29.58, 29.68, 32.21, 35.36, 48.78, 48.97, 71.43, 71.73, 73.85, 74.30, 172.52, 173.71. Anal Calculated for C$_{30}$H$_{60}$N$_2$O$_6$: C, 67.09; H, 11.26, N, 4.89. Found: C, 66.98; H, 11.38; N, 4.90.

Example 19

Synthesis of dioleyl D-glucaramide. D-Glucaric acid (lactone) (1.27 g, about 6.5 mmol) was added to a solution of oleylamine (3.87 g, 14.4 mmol) in EtOH (30 ml). After 20 hours stirring, the suspension was refluxed for 0.5 hour and recrystallized from EtOH (2×) and DMSO. Yield 0.72 g (1.4 mmol, 21%). $^1$H-NMR (d$_6$-DMSO, 300 MHz, ppm): δ 0.88 (t, 6H), 1.28 (in, 44H), 1.45 (m, 4H), 2.01 (m, 8H), 3.07 (bs, HDO+4H), 3.75 (m, 1H), 3.91 (m, 1H), 3.96 (m, 1H), 3.98 (m, 1H), 4.38 (bs, 1H), 4.52 (bs, 1H), 5.10 (bs, 2H), 5.35 (m, 4H), 7.32 (bs, 1H), 7.55 (bs, 1H). $^{13}$C-NMR (d$_6$-DMSO, 500 MHz, T=100° C., ppm): 14.36, 22.61, 27.04, 27.30, 27.34, 29.24, 28.28, 29.38, 29.44, 29.48, 29.62, 29.68, 29.76, 29.80, 31.88, 39.12, 39.20, 71.40, 72.67, 73.67, 73.86, 130.3, 172.68, 173.68. Anal Calculated for C$_{42}$H$_{80}$N$_2$O$_6$: C, 71.14; H, 11.37, N, 3.95. Found: C, 70.87; H, 11.43; N, 3.97.

Example 20

Synthesis of 3-O-methyl-dicyclohexyl D-glucaramide. 3-O-Methyl diethyl D-glucarate (0.54 g, 1.9 mmol) was added to a solution of cyclohexylamine (0.48 g, 4.8 mmol) in EtOH (20 ml). After 20 hours stirring, the precipitate was filtered off. Yield 0.20 g (0.75 mmol, 39%). $^1$H-NMR (d$_6$-DMSO, 300 MHz, ppm): δ 1.26 (m, 10H), 1.70 (m, 10H), 3.32 (s, 3H), 3.59 (m, 2H), 3.65 (m, 1H), 3.74 (m, 1H), 3.89 (m, 1H), 4.08 (m, 1H), 4.78 (m, 1H), 5.45 (bs, 2H), 7.40 (d, 1H), 7.51 (d, 1H). $^{13}$C-NMR (d$_6$-DMSO, 300 MHz, ppm): 24.53, 26.13, 33.21, 48.20, 60.95, 72.35, 73.24, 74.51, 81.85, 172.00, 172.50. Anal Calculated for C$_{19}$H$_{34}$N$_2$O$_6$: C, 59.05; H, 8.87; N, 7.25. Found: C, 58.91; H, 8.90; N, 7.27.

Example 21

Synthesis of 3-O-methyl-didodecyl D-glucaramide. 3-O-Methyl diethyl D-glucarate (0.60 g, 2.1 mmol) was added to a solution of cyclododecylamine (0.93 g, 5.0 mmol) in EtOH (20 ml). After 72 hours stirring, the precipitate was filtered off and crystallized from EtOH. Yield 0.55 g (0.98 mmol, 46%). $^1$H-NMR (d$_6$-DMSO, 300 MHz, T=100° C., ppm): δ 0.84 (t, 6H), 1.26 (m, 36H), 1.45 (m, 4H), 3.34 (s, 3H), 3.70 (m, 1H), 3.80 (m, 1H), 3.95 (m, 1H), 4.09 (m, 1H), 4.58 (bs, 1H), 5.03 (bs, 2H), 7.32 (bs, 1H), 7.42 (bs, 1H). $^{13}$C-NMR (d$_6$-DMSO, 300 MHz, T=100° C., ppm): 14.08, 22.38, 26.83, 29.03, 29.16, 28.38, 31.66, 38.97, 60.02, 72.06, 72.72, 73.91, 81.39, 172.37, 173.15. Anal Calculated for C$_{31}$H$_{62}$N$_2$O$_6$: C, 66.63; H, 11.18, N, 5.01. Found: C, 66.63; H, 11.33; N, 5.04.

Example 22

Synthesis of 3-O-methyl-dicyclododecyl D-glucaramide. 3-O-Methyl diethyl D-glucarate (0.60 g, 2.1 mmol) is added to a solution of cyclododecylamine (0.98 g, 5.3 mmol) in EtOH (20 ml). After 20 hours stirring, the precipitate was filtered off and crystallized from EtOH. Yield 0.30 g (0.54 mmol, 25%). $^1$H-NMR (d$_6$-DMSO, 300 MHz, T=100° C., ppm): δ 1.33 (m, 36H), 1.57 (m, 8H), 3.35 (s, 3H), 3.69 (bs, 1H), 3.77 (bs, 1H), 3.93 (bs, 3H), 4.09 (bs, 1H), 4.47 (bs, 1H), 5.03 (bs, 2H), 7.02 (d, 1H), 7.12 (d, 1H). $^{13}$C-NMR (d$_6$-DMSO, 300 MHz, T=100° C., ppm): 22.02, 23.97, 24.16, 30.61, 45.52, 60.06, 71.91, 72.62, 72.76, 73.86, 81.43, 171.71, 172.42. Anal Calculated for C$_{31}$H$_{58}$N$_2$O$_6$: C, 67.11; H, 10.54, N, 5.05. Found: C, 65.64; H, 10.44; N, 5.00.

Example 23

Synthesis of N$_1$-cyclododecyl, N$_6$-cyclohexyl D-glucaramide. Cyclohexylammonium 6-(N-cyclohexyl)-D-glucaramide-1-ate (0.60 g, 2.1 mmol) was added to a solution of Dowex H$^+$(1×8) in H$_2$O (40 ml). After 30 minutes stirring the suspension is filtered and washed thoroughly with H$_2$O. The filtrate was evaporated and the crude 6-(N-cyclohexyl)-D-glucaramide (lacton) was added to a solution of p-toluene sulfonic acid (0.038 g, 0.20 mmol) in EtOH (20 ml). At T=50° C. cyclododecylamine (0.47 g, 2.6 mmol) was dropped slowly to the solution. After one hour stirring the solution was cooled to T=4° C. and recrystallized from DMSO/H$_2$O. Yield 0.13 g (0.33 mmol, 13%). $^1$H-NMR (d$_6$-DMSO, 300 MHz, T=100° C., ppm): 1.13–1.75 (m, 32H), 3.59 (bs, 1H), 3.70 (m, 1H), 3.92 (m, 1H), 3.94 (m, 2H), 3.99 (m, 1H), 4.49 (bs, 1H), 4.63 (bs, 1H), 5.20 (bs, 1H), 5.33 (bs, 1H), 7.13 (bs, 1H), 7.45 (bs, 1H). $^{13}$C-NMR (d$_6$-DMSO, 300 MHz, T=95° C., ppm): 22.20, 22.27, 24.20, 24.38, 25.05, 25.89, 30.86, 32.80, 32.84, 45.65, 48.15, 71.41, 72.68, 73.65, 73.90, 172.05, 172.80.

Example 24

Solvent scope of N,N'-dialkylaldaramides (1%) or N,N'-dialkylpentaramides (1%) 1–24 refers to the compounds prepared in Examples 1–23)

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| Hexadecane | ns | Ns | ns | ns | ns | — | ns | ns | ns | ns | p | ns | ns | ns | ns | ns | ns | s | p | ns | p | ns | — |
| Cyclohexane | ns | Ns | ns | ns | G | ns | ns | ns | ns | ns | g* | ns | ns | ns | g | ns | ns | s | p | ns | g | g | p |
| p-xylene | ns | Ns | ns | p | G | — | ns | ns | ns | p | ns | ns | ns | g | ns | ns | s | p | p | p | p | p |
| Toluene | ns | Ns | ns | p | G | ns | ns | ns | ns | p | ns | ns | ns | g | ns | ns | s | p | p | p | p | — |
| n-butylacetate | ns | Ns | ns | p | G | ns | ns | ns | ns | ns | p | ns | ns | ns | g | ns | ns | s | c | p | c | p | p |
| 1,2-dichloroethane | ns | Ns | ns | s | cg | p | ns | ns | ns | ns | s | p | c | ns | g | c | ns | s | c | c | p | p | — |

-continued

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| 2-octanol | P | Ns | ns | p | cg | — | ns | ns | ns | ns | s | ns | p | ns | s | s | ns | s | c | p | c | p | — |
| 2-propanol | C | C | c | p | cg | — | c | c | c | ns | s | ns | c | ns | c | cg | ns | s | c | c | p | p | — |
| Ethanol | C | C | c | s | cg | — | c | c | c | c | s | p | ns | ns | cg | p | ns | s | c | c | p | p | — |
| Dimethylsulfoxide | S | C | s | s | cg | — | c | s | c | s | s | s | c | ns | cg | p | ns | s | c | c | s | p | — |
| Water | ns | Ns | ns | ns | ns | — | ns | ns | ns | ns | c | ns | ns | ns | ns | ns | ns | p | ns | ns | ns | — | — |
| silicon oil | — | — | — | -- | G | — | — | — | — | — | — | — | — | — | g | — | ns | s | — | — | v | — | v |
| methyl laurate | — | — | — | — | G | — | — | — | — | — | — | — | — | — | g | — | ns | s | — | — | — | — | p |
| methyl benzoic acid | — | — | — | — | S | — | — | — | — | — | — | — | — | — | g | — | ns | s | — | — | p | — | p |
| 2-methoxyethanol | — | — | — | — | S | — | — | — | — | — | — | — | — | — | c | — | ns | s | — | — | — | — | p | g = gelation, s = soluble, p = precipitates, c = crystallizes, ns = not soluble, v = viscous, g* = unstable gel, precipitates, cg = crystalline gel

Example 25

Gelation of N,N'-dialkyladaramides (1%) in Mixtures of Solvents

|  | 11 (cit-Glu-cit) | 12 (12-Glu-12) | 15 (C12-Glu-C12) |
|---|---|---|---|
| cyclohexane | g* | ns | g |
| cyclohexane/dioxane 1:1 | s | — | cg |
| Dioxane | s | c | cg |
| dioxane/H$_2$O 3:1 | s | c | cg |
| dioxane/H$_2$O 2:1 | s | c | cg |
| dioxane/H$_2$O 1:1 | p | ns | g |
| dioxane/H$_2$O 1:2 | p | ns | ns |
| H$_2$O | c | ns | ns | g = gelation, s = soluble, p = precipitates, c = crystallizes, ns = not soluble, g* = unstable gel, precipitates, cg = crystalline gel

Example 26

Addition of a solution of the gelling agent (10% in NMP, 0.05 ml) to an organic solution (0.5 ml, "cold gelation")

|  | 5 (C6-Glu-C6) | 12 (12-Glu-12) | 15 (C12-Glu-C12) | 18 (B13-Glu-B13) |
|---|---|---|---|---|
| cyclohexane | p | p | g | s |
| methyl laurate | c | p | g | s |
| Toluene | c | p | g | s |
| n-butyl acetate | c | p | g | s |
| 1,2-dichloroethane | c | p | c | s |
| silicon oil | — | — | g | — |
| Acetone | — | — | cg | — |
| benzaldehyde | — | — | s | — |
| Chloroform | — | — | s | — |
| diethyl ether | — | — | g | — |
| ethylacetate | — | — | p | — |
| Heptane | — | — | p | — |
| Hexane | — | — | p | — |
| Acetonitril | — | — | g | — |
| tetrahydrofuran | — | — | c | — |

Example 27

Maximum gelator concentration of 5 (C6-Glu-C6) and 15 (C12-Glu-C12)

|  | 5 (in %) (C6-Glu-C6) | 15 (in %) (C12-Glu-C12) |
|---|---|---|
| cyclohexane | <5 | <5 |
| methyl laurate | <2.5 | <5 |
| silicon oil (Dow Corning 702) | <2.5 | <50 |
| Toluene | <2.5 | <50 |
| n-butylacetate | <2.5 | <50 |
| 1,2-dichloroethane | <5 | <50 |

Example 28

Phase Diagram of 5 (C6-Glu-C6) and 15 (C12-Glu-C12)) Dropping Ball Method)

The phase diagram of 5 (C6-Glu-C6) and 15 (C12-Glu-C12) was determined (see FIG. 1) by using the dropping ball method (A. Takashi, M. Sakai, T. Kato, *Polym. J.*, 12 (1980) 335–341, F. S. Schoonbeek, J. H. van Esch, R. Hulst, R. M. Kellogg, B. L. Feringa, *Chem. Eur. J.*, 6 (2000) 2633–2643). A linear correlation was observed between the $T_m^{-1}$ and the logarithm of the mole fraction of 15 (C12-Glu-C12) in cyclohexane, silicon oil and p-xylene, as expected for the dissolution process of crystals (gels) (K. Murata, M. Aoki, T. Suzuki, T. Harada, H. Kawabata, T. Komori, F. Ohseto, S. Shinkai, *J. Am. Chem. Soc.*, 116 (1994) 6664–6676).

What is claimed is:

1. A gelling agent or thickener in the form of a N,N'-disubstituted aldaramide, a N,N'-disubstituted pentaramide, or a derivative thereof having the formula

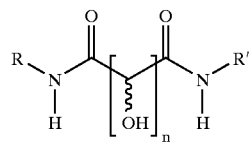

wherein n is 3 or 4, and wherein R and R' represent the same or different substituents selected from the group of substituted or unsubstituted cycloalkyl groups having up to 40 carbon atoms.

2. The gelling agent or thickener of claim 1, wherein R and R' each are independently selected from the group of cycloalkyl grous having 4–20 carbon atoms.

3. The gelling agent or thickener of claim 2, wherein R and R' each are independently selected from cyclohexyl and cyclododecyl.

4. The gelling agent or thickener of claim 1, wherein R and R' are the same.

5. The gelling agent or thickener of claim 1 being an N,N'-dicycloalkyl D-glucaramide.

6. A process for preparing the gelling agent or thickener of claim 1, said process comprising:

oxidation of an aldose or pentose to form an aldaric or pentaric acid or a salt thereof, and condensation of the aldaric or pentaric acid or the salt thereof with a primary amine of the formula $RNH_2$ and a primary amine of the formula $R'NH_2$.

7. The process of claim 6, wherein the aldaric or pentaric acid or salt thereof is activated before condensation by lactonization and/or esterification.

8. The process of claim 6 wherein the aldose or pentose is selected from the group consisting of allose, altrose, glucose, mannose, gulose, idose, galactose, talose, ribose, arabinose, xylose, lyxose, and derivatives thereof.

9. The process of claim 8, wherein the derivative is a deoxy aldose or pentose, an ether, or an ester.

10. The process of claim 7 wherein the aldose or pentose is selected from the group consisting of allose, altrose, glucose, mannose, gulose, idose, galactose, talose, ribose, arabinose, xylose, lyxose, and derivatives thereof.

11. The process of claim 10, wherein the derivative is a deoxy aldose or pentose, an ether, or an ester.

12. A process for preparing a gel or thickened composition comprising:

mixing the gelling agent or thickener of claim 1 with a composition, thus transforming the composition into a gel or thickened composition.

13. The process of claim 12, wherein the composition comprises an organic solvent.

14. The process of claim 13 wherein the solvent is selected from the group consisting of aromatic and non-aromatic hydrocarbons, alcohols, ethers, esters, aldehydes, alkanoic acids, epoxides, amines, halogenated hydrocarbons, silicon, vegetable oils, phosphoric esters, sulfoxides, water and mixtures thereof.

15. The process of claim 12 wherein the gelling agent or thickener is mixed with the composition in a ratio of between about 0.01 and about 50% by weight.

16. The process of claim 14 wherein the mixture of the gelling agent or thickener and the composition is heated, or wherein a solution of the gelling agent or thickener is added to or sprayed into the composition.

17. The process of claim 15 wherein the mixture of the gelling agent or thickener and the composition is heated, or wherein a solution of the gelling agent or thickener is added to or sprayed into the composition.

18. A gel comprising the gelling agent or thickener of claim 1.

19. A gel produced by the process of claim 12.

* * * * *

UNITED STATES PATENT AND TRADEMARK OFFICE
CERTIFICATE OF CORRECTION

PATENT NO. : 6,930,203 B2
APPLICATION NO. : 10/656839
DATED : August 16, 2005
INVENTOR(S) : Johannes Henricus van Esch and André Heeres It is certified that error appears in the above-identified patent and that said Letters Patent is hereby corrected as shown below:

CLAIM 2, COLUMN 12, LINE 62, change "grous" to --groups--

Signed and Sealed this

Tenth Day of April, 2007

JON W. DUDAS
*Director of the United States Patent and Trademark Office*